United States Patent [19]

Rasberger et al.

[11] 4,026,866

[45] * May 31, 1977

[54] NICKEL STABILIZERS FOR SYNTHETIC POLYMERS

[75] Inventors: Michael Rasberger, Allschwil; Johann Rody, Basel; Paul Moser, Riehen; Helmut Müller, Binningen, all of Switzerland

[73] Assignee: Ciba-Geigy Corporation, Ardsley, N.Y.

[*] Notice: The portion of the term of this patent subsequent to Aug. 26, 1992, has been disclaimed.

[22] Filed: June 13, 1975

[21] Appl. No.: 586,826

Related U.S. Application Data

[62] Division of Ser. No. 370,180, June 14, 1973, Pat. No. 3,901,931.

[30] Foreign Application Priority Data

June 21, 1972 Switzerland .................. 9333/72

[52] U.S. Cl. .................. 260/45.75 N; 260/242; 260/270 R; 260/439 R
[51] Int. Cl.$^2$ .................................. C07F 15/04
[58] Field of Search .................. 260/439 R, 45.75 N

[56] References Cited

UNITED STATES PATENTS 3,189,630   6/1965   Smutny ................. 260/439 R
3,636,023   1/1972   Murray et al. .......... 260/439 R

FOREIGN PATENTS OR APPLICATIONS 991,591   5/1965   United Kingdom

Primary Examiner—Arthur P. Demers
Attorney, Agent, or Firm—Nestor W. Shust

[57] ABSTRACT

New complexes of nickel salts of hydroxybenzoic acids are stabilizers for polymers. The complexes are prepared by reacting a nickel benzoate with a corresponding alcohol.

11 Claims, No Drawings

NICKEL STABILIZERS FOR SYNTHETIC POLYMERS

This is a divisional of application Ser. No. 370,180 filed on June 14, 1973, now U.S. Pat. No. 3,901,931.

The invention relates to new nickel complexes of hydroxybenzoic acids, their manufacture, their use as light stabilisers and/or as dyestuff receptors for polymer substrates, and, as industrial product, to the polymers which contain the claimed compounds.

The new compounds have the formula I

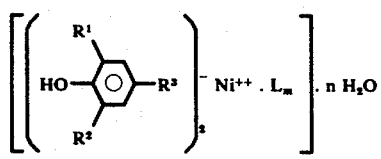 (I)

wherein
$R^1$ represents hydrogen or alkyl with 1 to 5 carbon atoms, and one of the substituents $R^2$ and $R^3$ represents an alkyl radical with 3 to 8 carbon atoms and the other represents $-COO^-$, $m$ is a number from 1 to 2, $n$ is a number from 0 to 2, and L is a ligand a. of the formula

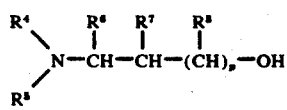

wherein
$R^4$ represents hydrogen, alkyl with 1 to 4 carbon atoms, cycloalkyl with 5 to 10 carbon atoms, aryl with 6 to 10 carbon atoms, or represents a radical of the formula

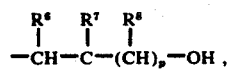

$R^5$ represents hydrogen, alkyl with 1 to 4 carbon atoms or the radical of the formula

or $R^4$ and $R^5$ together with the nitrogen atom represent the radical of a 5- or 6-membered heterocycle of the pyrrolidine, piperidine, piperazine, or morpholine series, $R^6$, $R^7$ and $R^8$ represents hydrogen or one of $R^6$, $R^7$ and $R^8$ represents alkyl with 1 to 4 carbon atoms, and $p$ is 0 or 1, or b. of the formula

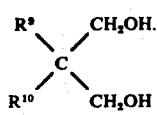

wherein
$R^9$ represents hydrogen, alkyl with 1 to 4 carbon atoms, $-OH$, $-NH_2$, $-CH_2OCH_2C(CH_2OH)_3$ or $-CH_2-OH$, and $R^{10}$ represents hydrogen, $-CH_2OH$ or alkyl with 1 to 4 carbon atoms, or c. of the formula

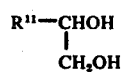

wherein
$R^{11}$ represents hydrogen, alkyl with 1 to 4 carbon atoms or $-CH_2OR^{12}$, and $R^{12}$ represents hydrogen, alkyl with 1 to 18 carbon atoms, or phenyl, or d. of the formula

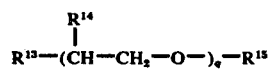

wherein
$R^{13}$ represents

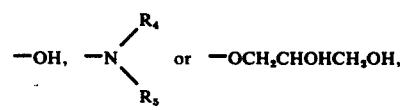

$R^{14}$ represents hydrogen or alkyl with 1 to 4 carbon atoms,
$R^{15}$ represents hydrogen or alkyl with 1 to 4 carbon atoms, and
$q$ is 2 or 3, or e. a mixture of the ligands cited under (a), (b), (c), and (d).

Preferred compounds are those of the formula I, wherein $R^1$ represents hydrogen or alkyl with 1 to 4 carbon atoms, and one of the substituents $R^2$ and $R^3$ represents an alkyl radical with 3 or 4 carbon atoms and the other represents $-COO^-$, $m$ is a number from 1 to 2, in particular 1 to 1,5, $n$ is a number from 0 to 2, in particular 0.3 to 0.8, and L represents a ligand a. of the formula

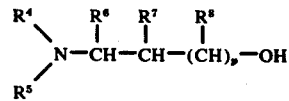

wherein
$R^4$ represents hydrogen, alkyl with 1 to 4 carbon atoms, cyclohexyl, phenyl, or a radical of the formula

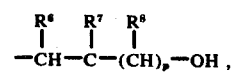

$R^5$ represents hydrogen, alkyl with 1 to 4, in particular, 1 or 2, atoms, or represents a radical of the formula

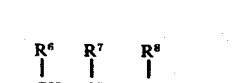

$R^4$ and $R^5$ together with the nitrogen atom represent the radical of a 5- or 6-membered, saturated heterocycle of the pyrrolidine, piperidine, piperazine, or morpholine series, $R^6$, $R^7$, and $R^8$ represent hydrogen or one of $R^6$, $R^7$, and $R^8$ represents methyl, and $p$ is 0 or 1, or b. of the formula

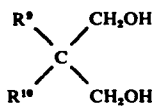

wherein R⁹ represents hydrogen, methyl, —OH, NH₂ or —CH₂OH, and R¹⁰ represents hydrogen, —CH₂OH or methyl, or c. of the formula

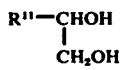

wherein R¹¹ represents hydrogen, alkyl with 1 to 4 carbon atoms, or —CH₂OR¹², and R¹² represents hydrogen, alkyl with 1 to 12, especially 8 to 12, carbon atoms, or represents phenyl, or d. of the formula

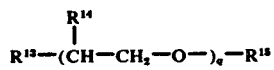

wherein
R¹³ represents

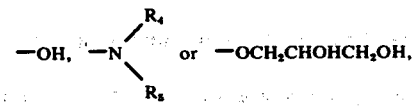

R¹⁴ represents hydrogen or methyl,
R¹⁵ represents hydrogen or ethyl, and $q$ is 2 or 3.
Particularly preferred compounds are those of the formula Ia

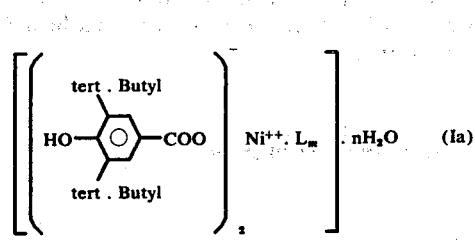

wherein
m is a number from 1 to 2 and n is a number from 0 to 2, and L is defined in the same manner as in the preferred compounds under (a) with p being 0, and in those under (b), (c), and (d).

The surprising discovery has been made that the compounds of the formula I, either as single compounds or as mixtures, are good stabilisers for polymers against light induced degradation and good colour receptors for chelatable dyestuffs.

It was already known to stabilise polyolefines with simple nickel benzoates. Compared with these salts, the new nickel complexes surprisingly possess a substantially better thermostability. They can therefore be processed at greatly elevated temperature without the polyolefines becoming discoloured as they are by the previously known nickel benzoates. It is known further to stabilise polyolefines by thiobisphenol-nickel-alkanolamine complexes. Compared with these compounds, the new nickel complexes display evidence of a much better light stability.

According to definition, R¹ to R¹², R¹⁴ and R¹⁵ can be alkyl groups. Within the limits indicated under the formula I these groups can be methyl, ethyl, n-propyl, isopropyl, n-butyl, sec. butyl, tert butyl, n-amyl, tert. amyl, n-hexyl, n-octyl, n-decyl, n-dodecyl n-tetradecyl, n-hexadecyl, or n-octadecyl.

Together with the nitrogen atom R⁴ and R⁵ can represent the radical of a heterocycle of the pyrrolidine series, e.g. pyrrolidine, 3-pyrrolidinol, of the piperidine series, e.g. piperidine, 2,6-dimethyl-piperidine, 4-hydroxy-piperidine, 4-methylpiperidine, of the piperazine series e.g. N-methyl-piperazine, piperazine, N-2-hydroxyethylpiperazine, or of the morpholine series, e.g. morpholine, 2,5- and 3,5-dimethylmorpholine.

The compounds of the formula I protect polymers against degradation, preferably α-olefine-polymers, e.g. polypropylene, optionally cross-linked polyethylene, polyisobutylene, polymethylbutene-1, polymethylpentene-1, polybutene-1, polyisoprene, polybutadiene; also polystyrene and copolymers thereof e.g. polyacrylonitrile-sytrene copolymers or polyacrylonitrile-butadiene-styrene copolymers; copolymers of the monomers based on the cited homopolymers, e.g. ethylene-propylene copolymers propylene-butene-1 copolymers, and terpolymers of ethylene and propylene with a diene, e.g. hexadiene, dicyclopentadiene or ethylidene-norbornene; mixtures of the above cited homopolymers, for example mixtures of polypropylene and polyethylene, polypropylene and polybutene-1, polypropylene and polyisobutylene. Preferred are polypropylene and its mixtures and the copolymers which contain the propylene units.

The compounds of the formula I are incorporated into the substrates in a concentration of 0.01 to 5% by weight, based on the material to be stabilised. Preferably 0.05 to 1.5, but more preferably still 0.1 to 0.8% by weight of the compounds, based on the material to be stabilised, is incorporated into it.

The incorporation can be effected after the polymerisation by blending at least one of the compounds of the formula I and optionally further additives into the melt by methods conventionally used in the art, either before or during the moulding, or also by applying the dissolved or dispersed compounds to the polymer, optionally with subsequent evaporation of the solvent.

The compounds of the formula I can also be incorporated into the polymer to be stabilised in the form of a master batch which contains the nickel stabiliser e.g. in a concentration of 2.5 to 25% by weight.

In the case of cross-linked polyethylene, the compounds are added before the cross-linking.

As further additives together with which it is possible to use the stabilisers, the following may be cited:
1. Antioxidants of the amino- and hydroxyaryl series. In the case of the latter, the sterically hindered phenol compounds may be cited, e.g.:
 2,2'-thiobis-(4-methyl-6-tert.butylphenol),
 4,4'-thiobis-(3-methyl-6-tert.butylphenol),
 2,2'-methylene-bis-(4-methyl-6-tert.butylphenol),
 2,2'-methylene-bis-(4-ethyl-6-tert.butylphenol,
 4,4'-methylene-bis-(2-methyl-6-tert.butylphenol),
 4,4'-butylidene-bis-(3-methyl-6-tert.butylphenol),
 2,2'-methylene-bis-[4-methyl-6-(α-methylcyclohexyl)-phenol],
 2,6-di-(2-hydroxy-3-tert.butyl-5-methylbenzyl)-4-methyl-phenol,
 2,6-di-tert. butyl-4-methylphenol, 1,1,3,-tris-2-methyl-(4-hydroxy-5-tert.butyl-phenyl)-butane, 1,3,5-trimethyl-2,4,6-tri-(3,5-di-tert.butyl-4-hydroxy-benzyl)-benzene, esters of β-4-hydroxy-3,5-di-tert.butylphenyl-propionic acid with mono- or polyvalent alcohols, such as methanol, ethanol, octadecanol, hexane diol, nonane diol, trimethylhexane diol, thiodiethylene glycol, trimethylol ethanes or pentaerythritol.

2,4-bis-octylmercapto-6-(4-hydroxy-3,5-di-tert-.butylanilino)-s-triazine, 2,4-bis-(4-hydroxy-3,5-di-tert.butylphenoxy)-6-octylmercapto-s-triazine, 1,1-bis-(4-hydroxy-2-methyl-5-tert.butyl-phenyl)-3-dodecylmercapto-butane, 4-hydroxy-3,5-di-tert.butylbenzyl-phosphonic ester, such as dimethyl-, diethyl- or dioctadecyl ester, (3-methyl-4-hydroxy-5-tert.butylbenzyl)-malonic acid -dioctadecyl ester, S-(3,5-dimethyl-4-hydroxyphenyl)-thioglycolic acid octadecyl ester, esters of bis-(3,5-di-tert.butyl-4-hydroxybenzyl)-malonic acid, such as didodecyl ester, dioctadecyl ester, 2-dodecylmercaptoethyl ester.

Among the aminoaryl derivatives, mention may be made of aniline and naphthylamine derivatives and their heterocyclic derivatives, e.g.:

Phenyl-1-naphthylamine,
phenyl-2-naphthylamine,
N,N'-diphenyl-p-phenylenediamine,
N,N'-di-2-naphthyl-p-phenylenediamine,
N,N'-di-sec.butyl-p-phenylenediamine,
6-ethoxy-2,2,4-trimethyl-1,2-dihydroquinoline,
6-dodecyl-2,2,4-trimethyl-1,2-dihydroquinoline,
mono- and dioctyliminodibenzyl,
polymerised 2,2,4-trimethyl-1,2-dihydroquinoline.

When using the compounds of the formula I in combination with the above cited amino compounds, it must be pointed out that, on account of the tendency of these latter to cause discolouration, the stabilised polymer no longer possesses such good color properties.

2. Ultraviolet absorbers and light filters, e.g.:

a. 2-(2'-hydroxyphenyl)-benztriazoles, for example the 5'-methyl-; 3',5'-di-tert.butyl; 5'-tert. butyl-; 5-chloro-3',5'di -tert.butyl-; 5-chloro-3' -tert.butyl-5'-methyl-; 3',5-di-tert.-amyl-; 3'methyl-5'-β-carbomethoxyethyl; 5-chloro-3',5-di-tert.amyl-derivative, b. 2,4-bis-(2'-hydroxyphenyl)-6-alkyl-s-triazines, e.g. the 6-ethyl or 6-undecyl derivative, c. 2-hydroxy-benzophenones, e.g. the 4-hydroxy, 4-methoxy, 4-octoxy, 4-decyloxy, 4-dodecyloxy, 4,2',-4'-tri-hydroxy or 2'-hydroxy 4,4'-dimethoxy derivative, d. 1,3-bis-(2'-hydroxy-benzoyl)-benzenes, e.g. 1,3-bis-('-hydroxy-4'-hexyloxy-benzoyl)-benzene, 1,3-bis-(2'-hydroxy-4'-octoxy-benzoyl)-benzene, 1,3-bis-(2'-hydroxy-4'-dodecyloxy-benzoyl)-benzene.

e. Aryl esters of optionally substituted benzoic acids, e.g. : phenylsalicylate, octylphenylsalicylate, di-benzoyl-resorcinol, benzoyl-resorcinol, 3,5.di-tert.butyl-4-hydrobenzoic acid-2,4-di-tert.butyl-phenyl or -octadecyl ester.

f. Acrylates, e.g.: α-cyano-β,β-diphenylacrylic acid ethyl- and isooctyl ester, α-carbomethoxy-cinnamic acidmethyl ester, α-cyano-β-methyl-p-methoxy-cinnamic acidmethyl and butyl ester, N-(β-carbomethoxy-vinyl)-2-methyl-indoline.

g. oxalic acid diamides, e.g. 4,4'-di-octyloxyocanilide, 2,2'-di-octyloxy-5,5'-di-tert.butyl-oxanilide, 2,2'-di-dodecyloxy-5,5'-di-tert.butyl-oxanilide, 3. Nucleination agents, e.g. 4-tert-butylbenzoic acid, adipic acid, diphenylacetic acid.

4. Compounds which decompose peroxide, e.g. esters of β-thiodipropionic acid, for example lauryl, stearyl, myrystyl or tridecyl ester, salts of 2-mercaptobenzimidazols, for example the zine salt, and diphenylthiourea.

5. Other additives, such as plasticisers, antistatic agents, dyeing assistants, flame-proofing agents, pigments, carbon black, asbestos, glass fibres, china clay, talcum, and flowing agents.

6. Costabilisers, e.g. salts of earth alkalies, preferably salts of earth alkalies and carboxylic acids, e.g. calcium stearate, calcium palmitate, calcium oleate, and calcium laurate.

The compounds according to the invention of the formula I

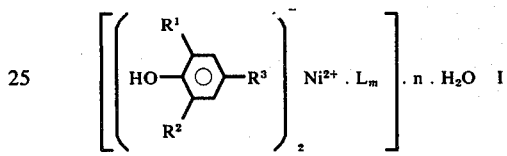

can be manufactured by various methods. For example, it is possible to dissolve 1 mole of the compound II

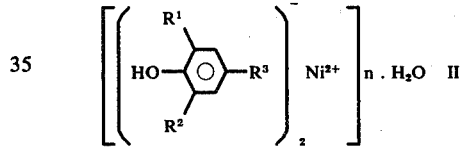

wherein $R^1$, $R^2$, and $R^3$ have the meanings given under the formula I, in an organic solvent, and with the application of heat to react the solution with ligands L, whose nature and composition are derived from the meaning given under the formula I, to give the compound I.

Suitable solvents for this reaction are chiefly alcohols, in particular methanol, ethanol, and isopropanol, ethylene glycol monomethyl ether, ethylene glycol monoethyl ether, dioxan, tetrahydrofuran, acetonitrile, and mixtures of these solvents.

A further possibility of obtaining compound I consists in refluxing compound II with ligands L in an organic solvent for a lengthy period of time over a steam trap.

For this process there are used accordingly solvents with the aid of which it is possible to distill off water azeotropically, for example benzene, toluene, xylene etc.

An end product with a specific amount of water bonded as a complex, i.e. with a specific value for n in formula I, is obtained by the first process by using a compound of the formula II with corresponding water content.

In both these above cited processes it is also possible to obtain a compound of the formula I with a specific amount of water bonded as a complex, so that at the termination of the reaction the isolated complex is dried until the analytical data indicate the correct composition. If required, any water which is lacking can be added before the isolation of the complex.

The manufacture of compounds of the formula II is described in U.S. Pat. No. 3,189,690.

The following Examples describe the invention in more detail, the parts and percentages being by weight.

EXAMPLE 1

A solution of 28.7 parts of Ni-3,5-di-tert.butyl-4-hydroxybenzoate, which contains 2.36% of water bonded as a complex, in 250 ml of absolute ethanol is treated dropwise with 7.5 parts of triethanolamine in 100 ml of absolute ethanol. The mixture is stirred for 15 hours at room temperature and subsequently refluxed for 2 hours. The solvent is distilled off in vacuo and the green residue is then dried for 20 hours at 60° C and 15 mbar. The complex consisting of 1 mole of Ni-benzoate, 1 mole of triethanolamine, and water has the following composition :
Calc. Ni 8.0%
(on 1.19% water content).
found: Ni 8.16%.
found: $H_2O$ 1.19%.

The following compounds were manufactured in analogous manner :

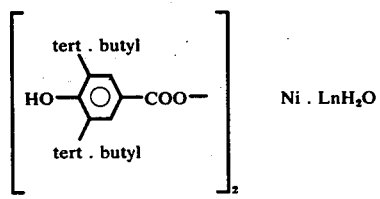

| No. | Ligand L | Calc Ni in % | Found Ni in % | $H_2O$ in % |
|---|---|---|---|---|
| 2 | $NH(CH_2CH_2OH)_2$ | 8,94 | 8,36 | 0,95 |
| 3 | $NH_2CH_2CH_2OH$ | 9,42 | 9,00 | 1,15 |
| 4 | $(CH_3)_2NCH_2CH_2CH_2OH$ | 8,80 | 8,66 | 1,0 |
| 5 | $CH_3NHCH_2CH_2OH$ | 9,16 | 8,97 | 1,34 |
| 6 | $(CH_3)_2NCH_2CH_2OH$ | 8,98 | 8,72 | 1,10 |
| 7 | $C_4H_5N(CH_2CH_2OH)_2$ | 8,13 | 8,01 | 1,25 |
| 8 | $H_2NCH_2CH_2CH_2OH$ | 9,20 | 9,17 | 0,98 |
| 9 | $(CH_3)_2NCH_2CHOHCH_3$ | 8,74 | 8,51 | 1,18 |
| 10 | $N(CH_2CHOHCH_3)_3$ | 7,77 | 7,38 | 1,01 |
| 11 | $Ph-N(CH_2CH_2OH)_2$ | 7,86 | 7,54 | 1,20 |
| 12 | ⬡NCH$_2$CH$_2$OH | 8,47 | 8,37 | 1,16 |
| 13 | HN⬡NCH$_2$CH$_2$OH | 8,46 | 8,05 | 1,58 |
| 14 | $H_2NC(CH_2OH)_3$ | 8,54 | 8,31 | 1,42 |
| 15 | Ph\\CH$_3$CH$_2$/NCH$_2$CH$_2$OH | 8,04 | 7,83 | 1,08 |
| 16 | HOCH$_2$CH$_2-$N⬡NCH$_2$CH$_2$OH | 7,92 | 7,59 | 1,30 |
| 17 | $H_2NCH_2CH_2OCH_2CH_2OH$ | 8,71 | 8,57 | 1,78 |
| 18 | $Ph-NHCH_2CH_2OH$ | 8,36 | 8,09 | 1,22 |
| 19 | $HOCH_2CHOHCH_2OH$ | 8,80 | 9,01 | 1,02 |
| 20 | $C_8H_{17}OCH_2CHOHCH_2OH$ | 7,65 | 7,40 | 0,93 |
| 21 | $C_{12}H_{25}OCH_2CHOHCH_2OH$ | 7,12 | 6,80 | 0,77 |
| 22 | $CH_3CH_2(OCH_2CH_2)_2-$ $-OCH_2CHOHCH_2OH$ | 7,57 | 7,38 | 1,00 |

Ph represents phenyl

EXAMPLE 2

A mixture of 57.3 parts of Ni-3,5-di-tert.butyl-4-hydroxybenzoate, which contains 2.36% of water bonded as a complex, 29.8 parts of triethanolamine, and 250 ml of benzene is refluxed for 20 hours over a steam trap. The solvent is distilled off and the residue is dried for 20 hours at 60° C and 15 mbar. The complex consisting of 1 mole of Ni-benzoate, 2 moles of triethanolamine, and water has the following composition :
Calc. N 6.8%
(on 1.19% water content).
found: N 6.41%.
found: $H_2O$ 0.37%.

EXAMPLE 3

1000 parts of polypropylene powder [melt index 1.5 g/10 minutes(230° C 2160g)] are mixed in a drum mixer with 0.5 part of tetrakis-β(3,5-di-tert.butyl-4-hydroxyphenyl)propionic acid pentaerythritol ester, 3 parts of dilaurylthio-dipriopionate (DLTDP) and 5 parts of a UV rays absorbing agent of the following Table and subsequently homogenised at 200° C for 10 minutes in a Brabender plastograph. The polymer substance is then pressed for 6 minutes at 240° C in a heated press to 1 mm thick sheets.

A visual evaluation of the test specimens for their discolouration gives the following results:

| No. | UV rays absorbing agent | Appearance of the sheet after 6 mins. at 240° C |
|---|---|---|
|  | (without ligand with 2.36% water content). | grey discolouration |
| 1 |  | no discolouration |
| 2 |  | no discolouration |
| 3 |  | faint grey tinge |
| 4 |  | no discolouration |
| 7 |  | no discolouration |
| 10 |  | faint grey tinge |
| 11 |  | no discolouration |
| 19 |  | no discolouration |
| 21 |  | no discolouration |

EXAMPLE 4

1000 parts of polypropylene powder [melt index 1.5 g/10 minutes (230° C, 2160 g)]are mixed in a drum mixer with 1 part of of β-(3,5-di-tert.-butyl-4-hydroxyphenyl)propionic acid octadecyl ester and 5 parts of a UV rays absorbing agent of the following Table and subsequently granulated at a temperature of 200° C in a Ko-kneader. The resulting granules are processed in the customary manner over an extruder with slot die to a sheet which is cut into ribbons which are subsequently stretched at elevated temperature in the stretch ratio 1:6 and wound up (titre of the ribbons : 700-900 den; ultimate tensile strength : 5.5-6.5 g/den).

The polypropylene ribbons are applied without tension to test carriers and exposed in a xenotest device 150. Five test specimens are taken after different times and their ultimate tensile strength is determined. The exposure time after which the ultimate tensile strength of the ribbons has declined to 50% of the starting value is taken as the criterion for the proctective action of the individual UV rays absorbing agents. The values obtained are listed in the following Table :

| No. | UV rays absorbing agent | | Hours of exposure to 50% ultimate tensile strength |
|---|---|---|---|
|  | 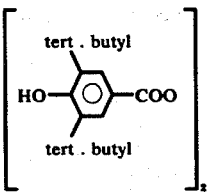 |  | (without 3850 ligand with 2.36% water content) |
| 1 |  |  | 3700 |
| 2 |  |  | 3600 |
| 3 |  |  | 4050 |
| 4 |  |  | 3700 |
| 7 |  |  | 3800 |
| 9 |  |  | 3650 |
| 11 |  |  | 3600 |
| 19 |  |  | 3500 |
| 20 |  |  | 4000 |
| 22 |  |  | 3700 |

We claim:
1. Compounds of the formula

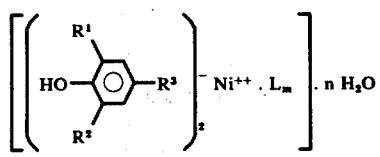                        (I)

wherein $R^1$ represents hyrogen or alkyl with 1 to 5 carbon atoms, and one of the substituents $R^2$ and $R^3$ represents an alkyl radical with 3 to 8 carbon atoms and the other represents —COO⁻, $m$ is a number from 1 to 2, $n$ is a number from from 0 to 2, and L is a ligand a. of the formula

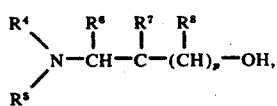

wherein $R^4$ represents hydrogen, alkyl with 1 to 4 carbon atoms, cycloalkyl with 5 to 10 carbon atoms, aryl with 6 to 10 carbon atoms, or represents a radical of the formula

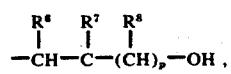

$R^5$ represents hydrogen, alkyl with 1 to 4 carbon atoms or the radical of the formula

$R^6$, $R^7$ and $R^8$ represent hydrogen or one of $R^6$, $R^7$ and $R^8$ represents alkyl with 1 to 4 carbon atoms, and $p$ is 0 or 1, or b. of the formula

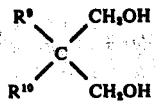

wherein $R^9$ represents hydrogen, alkyl with 1 to 4 carbon atoms, —OH, $NH_2$, —$CH_2OCH_2C(CH_2OH)_3$ or —$CH_2$—OH, and $R^{10}$ represents hydrogen, —$CH_2OH$ or alkyl with 1 to 4 carbon atoms, or c. of the formula

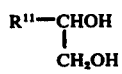

wherein $R^{11}$ represents hydrogen, alkyl with 1 to 4 carbon atoms or —$CH_2OR^{12}$, and $R^{12}$ represents hydrogen, alkyl with 1 to 18 carbon atoms, or phenyl, or d. of the formula

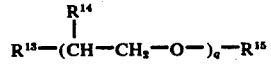

wherein $R^{13}$ represnts

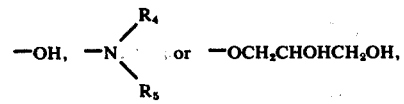

$R^{14}$ represents hydrogen or alkyl with 1 to 4 carbon atoms, $R^{15}$ represents hydrogen or alkyl with 1 to 4 carbon atoms, and $q$ is 2 or 3, or e. a mixture of the ligands cited under (a), (b), (c), and (d).

2. Compounds according to claim 1, wherein in formula I $R^1$ represents hydrogen or alkyl with 1 to 4 carbon atoms, and one of the substituents $R^2$ and $R^3$ represents an alkyl radical with 3 or 4 carbon atoms and the other represents —COO⁻, $m$ is a number from 1 to 2, $n$ is a number from 0 to 2, and L represents a ligand a. of the formula

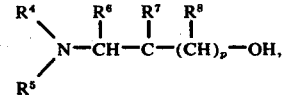

wherein $R^4$ represents hydrogen, alkyl with 1 to 4 carbon atoms, cyclohexyl, phenyl, or a radical of the formula

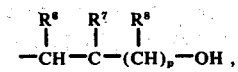

$R^5$ represents hydrogen, alkyl with 1 to 4 carbon atoms, or represents a radical of the formula

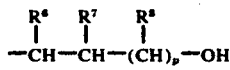

$R^6$, $R^7$, and $R^8$ represents hydrogen or one of $R^6$, $R^7$, and $R^8$ represents methyl, and $p$ is 0 or 1, or
b. of the formula

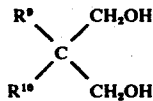

wherein $R^9$ represents hydrogen, methyl, —OH, $NH_2$ or —$CH_2OH$, and $R^{10}$ represents hydrogen, $CH_2OH$ or methyl, or
c. of the formula

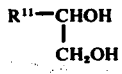

wherein $R^{11}$ represents hydrogen, alkyl with 1 to 4 carbon atoms, or —$CH_2OR^{12}$, and $R^{12}$ represents hydrogen, alkyl with 1 to 12 carbon atoms, or represents phenyl, or
d. of the formula

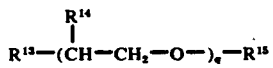

wherein $R^{13}$ represents

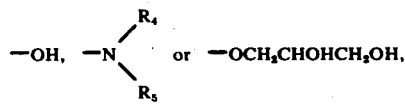

$R^{14}$ represents hydrogen or methyl, $R^{15}$ represents hydrogen or ethyl, and $q$ is 2 or 3.

3. Compounds according to claim 1, of the formula Ia

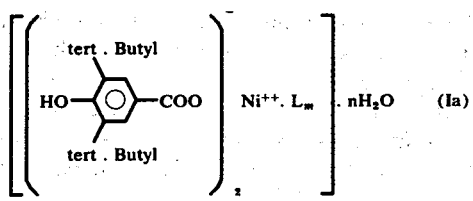

wherein $m$ is a number from 1 to 2, $n$ is a number from 0 to 2, L is a ligand
a. of the formula

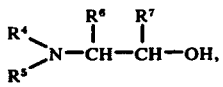

wherein $R^4$ represents hydrogen, alkyl with 1 to 4 carbon atoms, cyclohexyl, phenyl, or a radical of the formula

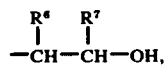

$R^5$ represents hydrogen, alkyl with 1 to 4 carbon atoms, or a radical of the formula

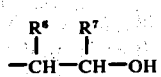

$R^6$, and $R^7$, represent hydrogen or one of $R^6$ and $R^7$, represents methyl, or
b. of the formula

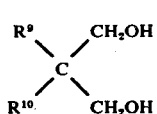

wherein $R^9$ represents hydrogen, methyl, —OH, —$NH_2$, or —$CH_2OH$, and $R^{10}$ represents hydrogen, —$CH_2OH$, or methyl, or
c. of the formula

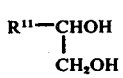

wherein $R^{11}$ represents hydrogen, alkyl with 1 to 4 carbon atoms, or —$CH_2OR^{12}$, and $R^{12}$ represents hydrogen, alkyl with 1 to 12 carbon atoms, or phenyl, or
d. of the formula

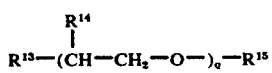

wherein $R^{13}$ represents

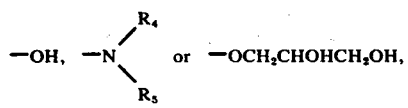

$R^{14}$ represents hydrogen or methyl, $R^{15}$ represents hydrogen or ethyl, and $q$ represents 2 or 3.

4. Compounds according to claim 1, of the formula I, wherein $R^1$ and $R^2$ represent tert. butyl, $R^3$, represents the radical —$COO^-$, $m$ is a number from 1 to 2, $n$ is a number from 0 to 2, L is a ligand
a. of the formula

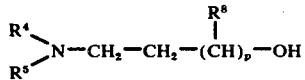

wherein $R^4$ represents hydrogen, alkyl with 1 to 4 carbon atoms, phenyl or a radical of the formula

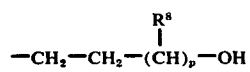

$R^5$ represents hydrogen, alkyl with 1 to 2 carbon atoms, or a radical of the formula

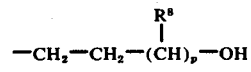

$R^8$ represents hydrogen or methyl, and $p$ is 0 or 1, b. of the formula

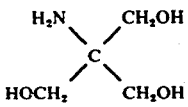

c. of the formula

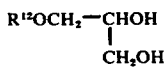

wherein $R^{12}$ represents hydrogen or alkyl with 8 to 12 carbon atoms, or d. of the formula

wherein $R^{13}$ represents $-NH_2$ or $-OCH_2CHOHCH_2OH$ and $R^{15}$ represents hydrogen or ethyl.

5. Compound according to claim 1 of the formula

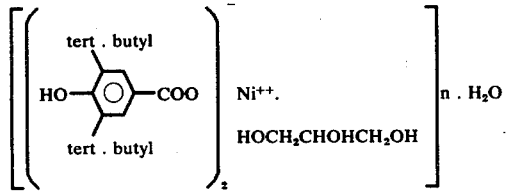

wherein $n$ is 0.37.

6. Compound according to claim 1, of the formula

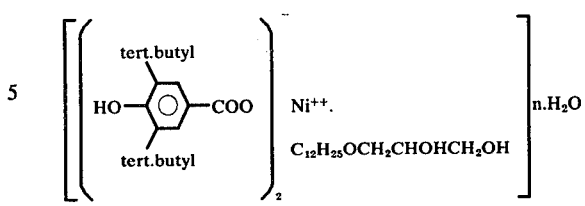

wherein $n$ is 0.37.

7. A composition of matter which comprises a polymer selected from the group consisting of α-olefin homopolymers and copolymers, polystyrene and copolymers thereof, and mixtures of the above-cited homopolymers and a compound of the formula I according to claim 1 in a concentration of 0.01 to 5% by weight, based on the material to be stabilized.

8. A composition of matter which comprises a polymer selected from the group consisting of α-olefin homopolymers and copolymers, polystyrene and copolymers thereof, and mixtures of the above-cited homopolymers and a compound of the formula I according to claim 2 in a concentration of 0.01 to 5% by weight, based on the material to be stabilized.

9. A composition of matter which comprises a polymer selected from the group consisting of α-olefin homopolymers and copolymers, polystyrene and copolymers thereof, and mixtures of the above-cited homopolymers and a compound of the formula I according to claim 3 in a concentration of 0.01 to 5% by weight, based on the material to be stabilized.

10. A composition of matter which comprises a polymer selected from the group consisting of α-olefin homopolymers and copolymers, polystyrene and copolymers thereof, and mixtures of the above-cited homopolymers and a compound of the formula I according to claim 4 in a concentration of 0.01 to 5% by weight, based on the material to be stabilized.

11. Compositions of matter according to claim 7, wherein the polyolefine is polypropylene.

* * * * *